US00PP31119P2

(12) United States Plant Patent
Wood

(10) Patent No.: US PP31,119 P2
(45) Date of Patent: Nov. 26, 2019

(54) ***SYRINGA* PLANT NAMED 'SMNSHSO'**

(50) Latin Name: ***Syringa* x *hyacinthaflora***
Varietal Denomination: SMNSHSO

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/350,435

(22) Filed: Nov. 15, 2018

(51) Int. Cl.
*A01H 5/00* (2018.01)

(52) U.S. Cl.
USPC ..... Plt./248

(58) Field of Classification Search
USPC ..... Plt./248
See application file for complete search history.

*Primary Examiner* — Annette H Para
(74) *Attorney, Agent, or Firm* — C. A. Whealy

(57) ABSTRACT

A new and distinct cultivar of *Syringa* plant named 'SMNSHSO', characterized by its relatively compact, upright to outwardly spreading and mounding plant habit; vigorous growth habit; freely branching habit; freely flowering habit; large inflorescences with fragrant light violet-colored flowers; and good garden performance.

2 Drawing Sheets

Botanical designation: *Syringa* x *hyacinthaflora*.
Cultivar denomination: 'SMNSHSO'.

BACKGROUND OF THE INVENTION

The present invention relates to a new and distinct cultivar of *Syringa* plant, commonly referred to as Lilac, botanically known as *Syringa* x *hyacinthaflora* and hereinafter referred to by the name 'SMNSHSO'.

The new *Syringa* plant is plant is a product of a planned breeding program conducted by the Inventor in Grand Haven, Mich. The objective of the breeding program is to create new compact *Syringa* plants with unique flower colors.

The new *Syringa* plant is a naturally-occurring whole plant mutation of a proprietary unnamed selection of *Syringa* x *hyacinthaflora*, not patented. The new *Syringa* plant was discovered and selected by the Inventor as a single flowering plant from within a population of plants of the mutation parent in a controlled environment in Grand Haven, Mich. in 2007.

Asexual reproduction of the new *Syringa* plant by softwood to semi-hardwood cuttings in a controlled greenhouse environment in Grand Haven, Mich. since 2011 has shown that the unique features of this new *Syringa* plant are stable and reproduced true to type in successive generations of asexual reproduction.

SUMMARY OF THE INVENTION

Plants of the new *Syringa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNSHSO'. These characteristics in combination distinguish 'SMNSHSO' as a new and distinct *Syringa* plant:

1. Relatively compact, upright to outwardly spreading and mounding plant habit.
2. Vigorous growth habit.
3. Freely branching habit.
4. Freely flowering habit.
5. Large inflorescences with fragrant light violet-colored flowers.
6. Good garden performance.

Plants of the new *Syringa* can be compared to plants of the mutation parent. Plants of the new *Syringa* differ primarily from plants of the mutation parent primarily in growth habit as plants of the new *Syringa* are more compact and smaller than plants of the mutation parent.

Plants of the new *Syringa* can be compared to plants of the *Syringa hybrida* 'Penda', disclosed in U.S. Plant Pat. No. 20,575. In side-by-side comparisons, plants of the new *Syringa* differ primarily from plants of 'Penda' in the following characteristics:

1. Plants of the new *Syringa* are more compact and shorter than plants of 'Penda'.
2. Plants of the new *Syringa* have larger flowers than plants of 'Penda'.

BRIEF DESCRIPTION OF THE PHOTOGRAPHS

The accompanying colored photographs illustrate the overall appearance of the new *Syringa* plant showing the colors as true as it is reasonably possible to obtain in colored reproductions of this type. Colors in the photographs may differ slightly from the color values cited in the detailed botanical description which accurately describe the colors of the new *Syringa* plant.

The photograph on the first sheet is a side perspective view of a flowering typical plant of 'SMNSHSO' grown in an outdoor nursery.

The photograph on the second sheet is a close-up view of a typical flowering typical plant of 'SMNSHSO'.

DETAILED BOTANICAL DESCRIPTION

Plants used for the following description were grown during the spring in three-gallon containers in a polyethylene-covered greenhouse in Grand Haven, Mich. and under cultural practices typical of commercial *Syringa* production. During the production of the plants, day temperatures ranged from 18° C. to 27° C. and night temperatures ranged from 5° C. to 10° C. Plants of the new *Syringa* were two years old when the photographs and description were taken. In the following description, color references are made to The Royal Horticultural Society Colour Chart, 2015 Edition, except where general terms of ordinary dictionary significance are used.

Botanical classification: *Syringa* x *hyacinthaflora* 'SMNSHSO'.

Parentage: Naturally-occurring whole plant mutation of a proprietary unnamed selection of *Syringa* x *hyacinthaflora*, not patented.

Propagation:

*Type*.—By softwood cuttings.

*Time to initiate roots, summer*.—About 20 days at temperatures about 18° C. to 27° C.

*Time to produce a rooted young plant, summer*.—About three months at temperatures about 18° C. to 27° C.

*Root description*.—Fine, fibrous; typically white in color, actual color of the roots is dependent on substrate composition, water quality, fertilizer, substrate temperature and physiological age of roots.

*Rooting habit*.—Freely branching; dense.

Plant description:

*Plant form and growth habit*.—Perennial shrub; relatively compact, upright to outwardly spreading and mounding plant habit; vigorous growth habit.

*Branching habit*.—Freely branching habit, about 20 lateral branches develop per plant.

*Plant height*.—About 70 cm.

*Plant diameter* (*area of spread*).—About 65 cm.

Lateral branch description:

*Length*.—About 18 cm.

*Diameter*.—About 4 mm.

*Internode length*.—About 2 cm to 3 cm.

*Aspect*.—Erect to about 45° from vertical.

*Strength*.—Strong.

*Texture*.—Smooth, glabrous.

*Color*.—Close to 199C.

Leaf description:

*Arrangement*.—Opposite, simple.

*Length*.—About 6 cm.

*Width*.—About 3.9 cm.

*Shape*.—Ovate.

*Apex*.—Acuminate.

*Base*.—Truncate.

*Margin*.—Entire.

*Texture, upper and lower surfaces*.—Smooth, glabrous.

*Venation pattern*.—Pinnate.

*Color*.—Developing leaves, upper and lower surfaces: Close to N199D. Fully expanded leaves, upper surface: Close to 143B; venation, close to 145B. Fully expanded leaves, lower surface: Close to 143C; venation, close to 145A.

*Petioles*.—Length: About 1.5 cm. Diameter: About 2 mm. Texture, upper and lower surfaces: Smooth, glabrous. Color, upper and lower surfaces: Close to N144D.

Flower description:

*Flower arrangement and flowering habit*.—Single salverform flowers arranged in terminal panicles; freely flowering habit with usually about 75 to 100 flowers developing per inflorescence; flowers face upright to outwardly.

*Natural flowering season and flower longevity*.—Plants of the new *Syringa* flower during the spring in Michigan; flowers not persistent.

*Fragrance*.—Moderately fragrant; fragrance sweet and pleasant.

*Inflorescence height*.—About 12.5 cm.

*Inflorescence diameter*.—About 10.2 cm.

*Flower diameter*.—About 1.9 cm.

*Flower length* (*height*).—About 1 cm.

*Flower throat diameter*.—About 2 mm.

*Flower tube length*.—About 9 mm.

*Flower tube diameter, proximally*.—About 1 mm.

*Flower buds*.—Length: About 4 mm. Diameter: About 6 mm. Shape: Obovate. Color: Close to N79D.

*Petals*.—Quantity and arrangement: Single whorl of four petals; lower portion of petals fused forming a narrow tube. Lobe length: About 9 mm. Lobe width: About 5 mm. Lobe shape: Elliptical. Apex: Acute. Margin: Entire. Texture, upper and lower surfaces: Smooth, glabrous, silky. Texture, throat and tube: Smooth, glabrous. Color: When opening, upper surface: Close to N80C. When opening, lower surface: Close to N80B. Fully opened, upper surface: Close to 85A; color does not fade with development. Fully opened, lower surface: Close to 85C; color does not fade with development. Throat: Close to 85C. Tube: Close to N88C.

*Sepals*.—Quantity and arrangement: Single whorl of four small sepals; fused towards the base forming a campanulate-shaped calyx. Length: About 1 mm. Width: Less than 1 mm. Shape: Narrowly deltoid. Apex: Acute. Margin: Entire. Texture, upper and lower surfaces: Smooth, glabrous. Color, upper and lower surfaces: Close to 181C.

*Peduncles*.—Length: About 1.8 cm. Diameter: About 1 mm. Strength: Moderately strong. Aspect: About 45° to 90° from the stem axis. Texture: Smooth, glabrous. Color: Close to 143A.

*Pedicels*.—Length: About 2 mm. Diameter: About 1 mm. Strength: Strong. Aspect: About 45° from peduncle axis. Texture: Smooth, glabrous. Color: Close to 143A.

*Reproductive organs*.—Androecium: Quantity of stamens per flower: Two. Filament length: About 1.5 mm. Filament color: Close to 201A. Anther length: About 2 mm. Anther shape: Oblong. Anther color: Close to 201A. Amount of pollen: Scarce. Pollen color: Close to 1A. Gynoecium: Quantity of pistils per flower: One. Pistil length: About 3 mm. Style length: About 2 mm. Style color: Close to 155A. Stigma shape: Oblong to rounded. Stigma color: Close to 155A. Seeds and fruits: To date, seed and fruit development have not been observed on plants of the new *Syringa*.

Garden performance: Plants of the new *Syringa* have been observed to have good garden performance and to tolerate rain, wind and temperatures ranging from about −32° C. to about 36° C.

Pathogen & pest resistance: To date, plants of the new *Syringa* have not been observed to be resistant to pathogens and pests common to *Syringa* plants.

It is claimed:

1. A new and distinct *Syringa* plant named 'SMNSHSO' as illustrated and described.

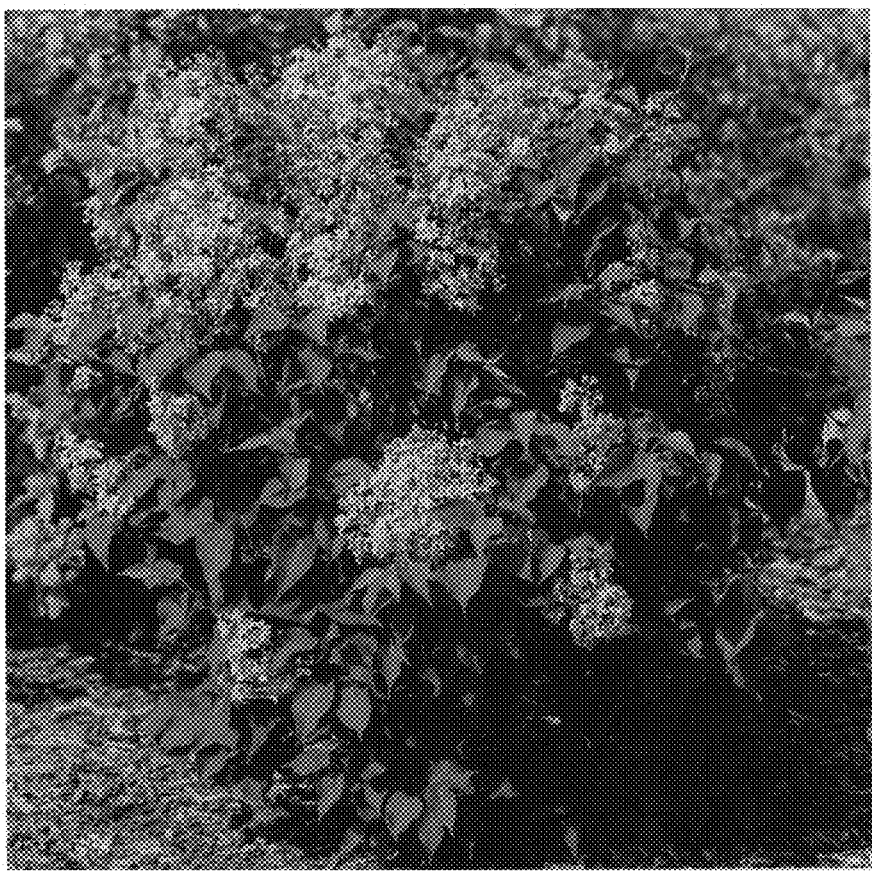

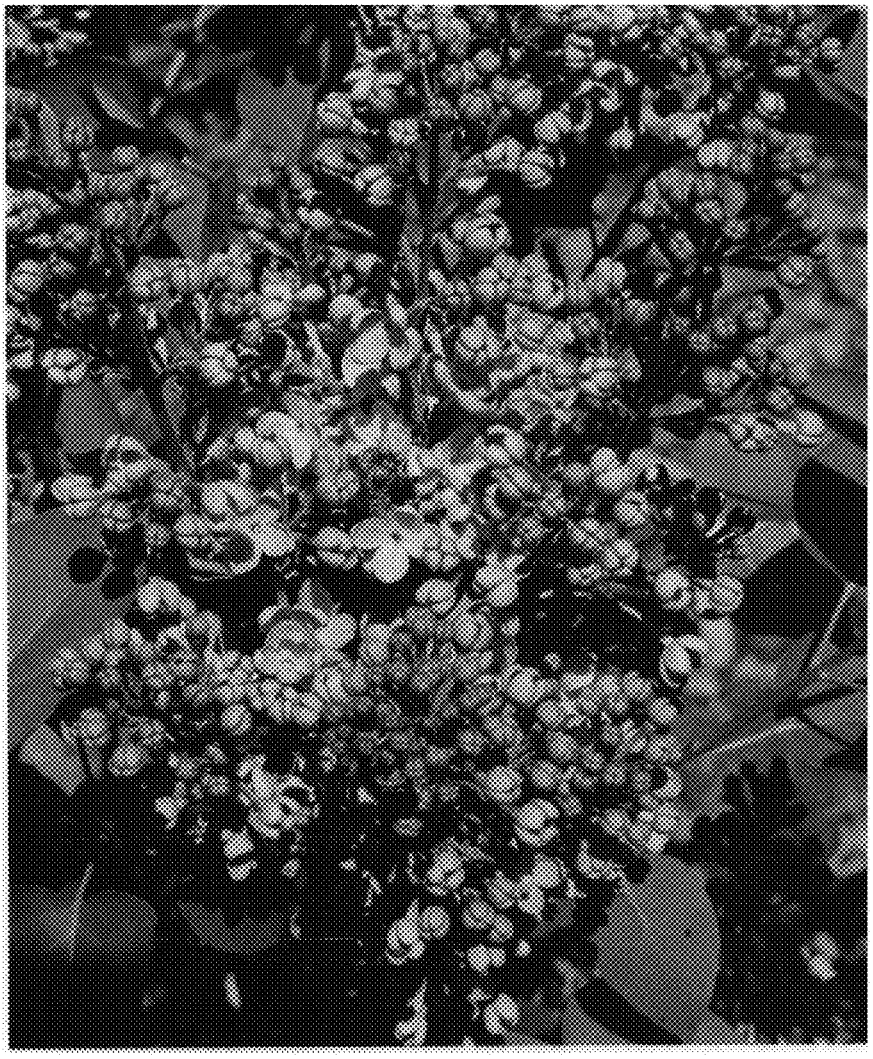

* * * * *